US005542913A

United States Patent [19]
Lindsay

[11] Patent Number: 5,542,913
[45] Date of Patent: Aug. 6, 1996

[54] IN-LINE QUICK CONNECT APPARATUS FOR MEDICAL FLUID CIRCULATING SYSTEMS

[75] Inventor: Erin J. Lindsay, Manchester, Mich.

[73] Assignee: Minnesota Mining and Manufacturing Company, St. Paul, Minn.

[21] Appl. No.: 316,245

[22] Filed: Sep. 30, 1994

Related U.S. Application Data

[63] Continuation-in-part of Ser. No. 77,344, Jun. 19, 1993, Pat. No. 5,399,156, which is a continuation-in-part of Ser. No. 493,491, Jun. 15, 1929, abandoned, which is a continuation-in-part of Ser. No. 493,286, Mar. 14, 1990, Pat. No. 5,149,318.

[51] Int. Cl.$^6$ ...................................................... B01D 19/00
[52] U.S. Cl. .................................................. 604/4; 604/403
[58] Field of Search ............................ 604/4, 5, 6, 317, 604/318, 319, 403, 405, 406, 905

[56] References Cited

U.S. PATENT DOCUMENTS

| | | |
|---|---|---|
| 3,585,995 | 6/1971 | Perkins et al. . |
| 3,678,959 | 7/1972 | Liposky . |
| 4,064,909 | 12/1977 | Neward . |
| 4,224,958 | 9/1980 | Kaplan et al. . |
| 4,306,705 | 12/1981 | Svensson . |
| 4,432,760 | 2/1984 | Mittleman et al. . |
| 4,440,723 | 4/1984 | Gordon . |
| 4,541,829 | 9/1985 | Munsch et al. . |
| 4,568,345 | 2/1986 | Keilman et al. . |
| 4,576,199 | 3/1986 | Svensson et al. . |
| 4,597,414 | 7/1986 | Johnson . |
| 4,617,012 | 10/1986 | Vaillancourt . |
| 4,664,682 | 5/1987 | Monzen . |
| 4,770,787 | 9/1988 | Heath et al. . |
| 4,822,341 | 4/1989 | Colone . |
| 4,846,800 | 7/1989 | Ouriel et al. . |
| 4,909,780 | 3/1990 | Ouriel et al. . |
| 4,988,342 | 1/1991 | Herweck et al. . |
| 5,047,011 | 9/1991 | Caron et al. . |
| 5,087,250 | 2/1992 | Lichte et al. . |
| 5,149,318 | 9/1992 | Lindsay . |
| 5,158,533 | 10/1992 | Strauss et al. . |
| 5,254,080 | 10/1993 | Lindsay . |
| 5,282,783 | 2/1994 | Lindsay . |
| 5,304,164 | 4/1994 | Lindsay . |
| 5,399,156 | 3/1995 | Lindsay ........................... 604/4 |

FOREIGN PATENT DOCUMENTS

| | | |
|---|---|---|
| 0312101 | 4/1989 | European Pat. Off. . |
| 2135890 | 9/1984 | United Kingdom . |
| WO91/0321 | 3/1991 | WIPO . |
| WO91/13640 | 9/1991 | WIPO . |

*Primary Examiner*—Sam Rimell
*Attorney, Agent, or Firm*—Gary L. Griswold; Walter N. Kirn; Stephen W. Bauer

[57] ABSTRACT

An in-line quick connect apparatus for the changeover of fluid lines in a medical fluid circulating system and systems incorporating the quick connect apparatus.

16 Claims, 3 Drawing Sheets

IN-LINE QUICK CONNECT APPARATUS FOR MEDICAL FLUID CIRCULATING SYSTEMS

CROSS-REFERENCE TO RELATED APPLICATIONS

This is a continuation-in-part of U.S. patent application Ser. No. 08/077,344 filed on Jun. 14, 1993, now U.S. Pat. No. 5,399,156, which is a continuation-in-part application of U.S. patent application Ser. No. 07/898,491 filed Jun. 15, 1992, now abandoned which is a continuation-in-part of U.S. patent application Ser. No. 07/493,286, filed Mar. 14, 1990, now U.S Pat. No. 5,149,318, all of which are hereby incorporated by reference.

FIELD OF THE INVENTION

The present invention relates to the connection and disconnection of fluid lines and their associated components in medical fluid circulating systems. More particularly, the present invention relates to an in-line quick connect apparatus for the changeover of fluid lines and associated components in a medical fluid circulating system.

BACKGROUND OF THE INVENTION

Changeovers between components in a blood circulating system using currently available products constitutes a very difficult and time consuming process during surgery. A typical blood circulating system includes a blood collection device, blood pump and heat exchanger/oxygenator assembly. The system may also include an arterial blood filter downstream from the heat exchanger/oxygenator unit. Such systems are used to oxygenate and circulate blood in a patient during heart surgery.

The heat exchanger/oxygenator assembly (with arterial blood filter, if present) must often be replaced during surgery. Reasons for replacement include leakage, clogging and/or other factors which cause the performance of the components to fall below allowable levels. Even in those situations in which the heat exchanger/oxygenator assembly is functioning properly, a different assembly may be substituted to provide a different function such as a hemodializer, etc.

One problem associated with replacement of a blood treatment assembly such as a heat exchanger/oxygenator or hemodializer is the potential for allowing air to enter the fluid lines connecting the devices. At the least, prime could be lost in the system requiring the operator to prime the system before restarting. At the worst, air in the system can cause strokes or death in patients should the air be allowed to enter the patient's bloodstream.

Another problem with replacement of the assembly is the complex and time-consuming procedure which must be performed to accomplish the changeover between assemblies. Such changeovers typically require the operators to: (a) stop the flow of the blood pump; (b) clamp all circuit lines to and from the components to be replaced; (c) drain all blood in the circuit lines into a reservoir; (d) remove the heat exchanger/oxygenator assembly from a mounting bracket; (e) remove the arterial blood filter, if present, from a mounting bracket; (f) mount the new heat exchanger/oxygenator assembly and arterial blood filter (if necessary); (g) prime the new components with saline solution; (h) open the clamped circuit lines; and (i) restart flow from the blood pump.

The above procedure typically takes four to ten minutes to complete. As a result, the cost to patients is increased along with an increase in patient morbidity due to the lengthened surgery time.

In addition to the increased time and complexity, the procedures also offer the opportunity for leakage of blood from the system due to improperly clamped circuit lines and/or unsealed ports on the components being removed. In many instances, the blood can be under pressure in the fluid lines, which increases the likelihood that it will leak or even spray from the fluid lines during changeovers. Exposure to blood is a significant concern for medical personnel as the blood can expose them to, among other diseases, hepatitis and AIDS. An additional problem is contamination of the circuit lines during the changeover procedure, as those lines must be reconnected before operation of the system can resume.

The present inventor's prior applications and issued patents, i.e., U.S. Pat. Nos. 5,149,318; 5,254,080, and 5,304,164 and 5,399,156 all of which are hereby incorporated by reference, have addressed issues surrounding conversion of devices which handle a patient's blood during surgery to devices which are useful during post-procedure care. As such, the apparatus described therein include connector blocks which can be replaced to convert the devices for different operations. Those connectors do not, however, offer the ability to replace components within the blood circulating system during an operation.

SUMMARY OF THE INVENTION

The present invention provides an in-line quick connect apparatus for the changeover of fluid lines in a medical fluid circulating system.

The apparatus provides for quick, sanitary changeovers of components in a medical fluid circulating system, substantially eliminating the risk of entraining air in the system, preventing the loss of prime in the system, and reducing the cost to the patient as well as patient morbidity by reducing the time required to perform changeovers.

The preferred apparatus also provides for automatic sealing of all fluid lines during changeovers, which prevents blood leakage from those lines, which may be under pressure, and the resulting exposure of medical personnel to blood-borne diseases such as hepatitis and AIDS.

In another aspect, the present invention comprises a medical fluid circulating system attached to a patient including a reservoir, blood pump and means for treating the patient's blood. The means for treating the blood is attached to the remainder of the system using an in-line quick connect apparatus according to the present invention, thereby providing the advantages discussed above.

Alternatively, any component or a number of components in the system could be connected using the apparatus according to the present invention. Any component thus connected could then also be replaced or removed from the system with all of the advantages discussed above.

These and other various features and advantages of the present invention will be apparent upon a reading of the claims and the detailed description, with reference to the drawings.

DETAILED DESCRIPTION OF THE PREFERRED EMBODIMENTS

Figure 1:
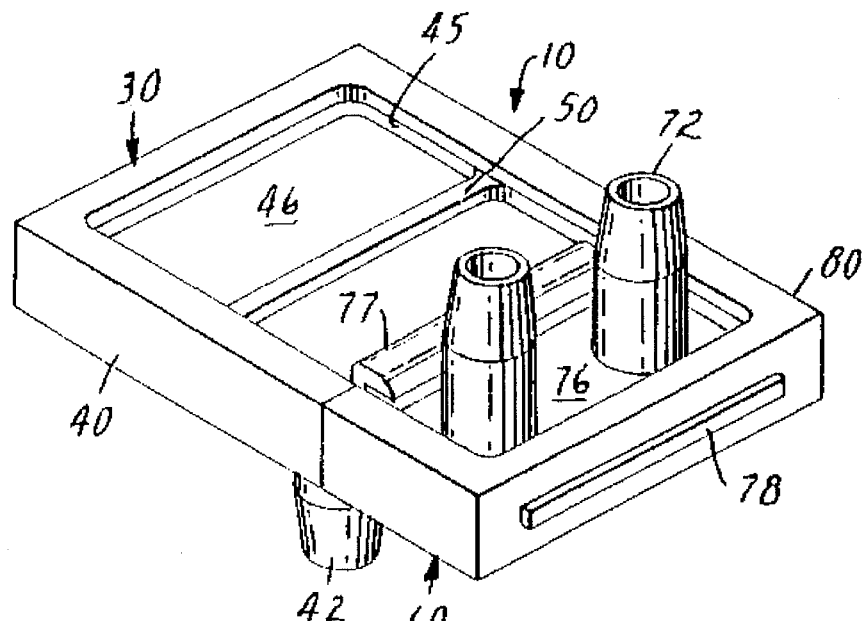
FIG. 1 is a perspective view of one embodiment of an in-line quick connect apparatus according to the present invention.
Figure 2:
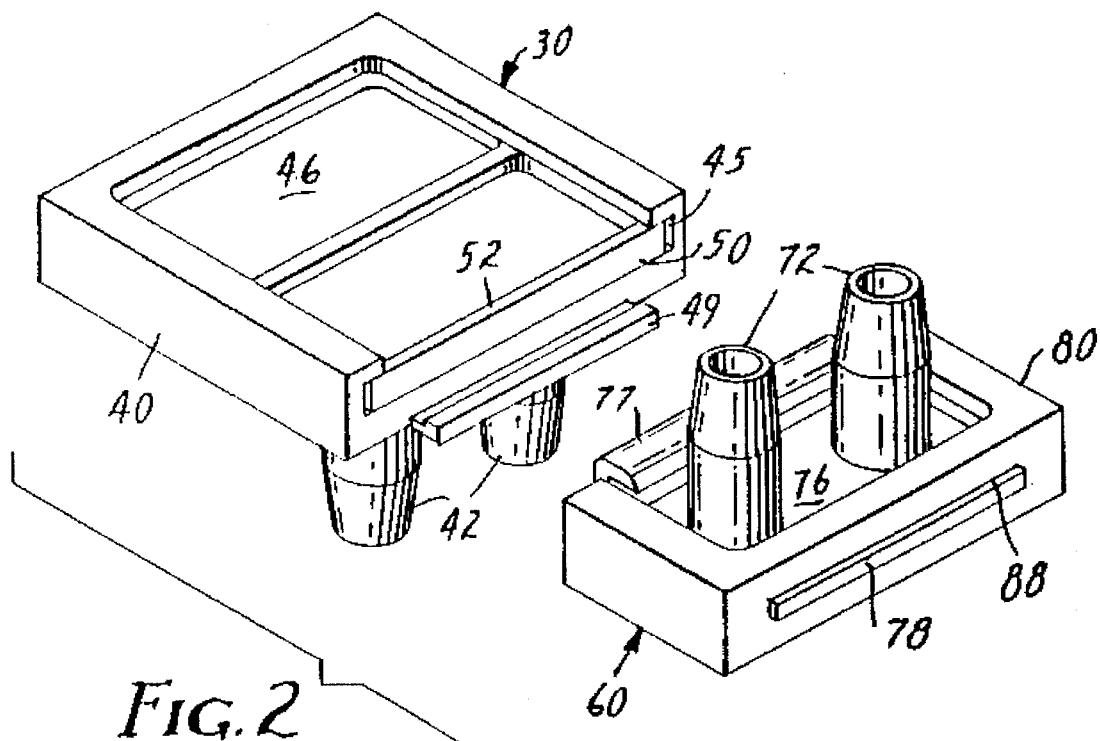
FIG. 2 is a partially exploded view of the apparatus of FIG. 1.

FIGS. 1-4 depict a preferred embodiment of the present invention which is useful for quick changeovers of components in blood circulating systems used during surgery. Although that application is the one described in detail below, it will be understood that the present invention may find applications in other situations involving the need for quick in-line changeovers of components connected by medical fluid lines and the description presented below is not intended to restrict the present invention, which is defined by the claims appended hereto.

Referring to FIGS. 1-4, in which a preferred embodiment is depicted in various stages of assembly, the apparatus 10 includes a connector 40 to which a seal tray 80 is removably attached.

Connector 40 includes two openings 44 (see FIG. 3) to which hose connectors 42 are attached. As a result, the openings 44 can be placed in fluid communication with hoses extending away from the apparatus 10.

Connector 40 also includes tracks 45 formed in the surface opposite that from which the hose connectors 42 extend. A seal 50 is located within the tracks 45 and slides between a first position shown in FIGS. 1 & 2 to a second position over the area indicated by reference number 46 on connector 40.

When in the first position over openings 44 in connector 40, the seal 50 preferably seals the openings 44 such that any fluid contained in hoses connected to hose connectors 42 is prevented from leaking out of holes 44 and the prime of the device attached to those hoses is not lost. To aid in sealing, the holes 44 are preferably surrounded by channels 47 sized to accommodate 0-ring seals (not shown). Rather than sealing each opening 44 individually, a single large O-ring or gasket extending around both openings 44 could be provided. Furthermore, the sealing gasket or O-ring could lie within a channel formed in seal 50 on its surface 54 which faces openings 44.

Other means and methods of sealing openings 44 using seal 50 will be well known to those skilled in the art. In some instances, the fit between the seal 50 and connector 40 could also be close enough such that no additional O-ring, gasket, etc. would be needed to prevent leakage and maintain prime within the components connected to the hoses attached to connectors 42.

Seal tray 80 is removably attached to connector 40. Seal tray 80 includes a second track means 85 sized and positioned to be aligned with the first track means 45 formed in the connector 40 when seal tray 80 is attached to connector 40.

Slide connector 70 is preferably fitted into seal tray 80 using tracks 85 formed therein. Slide connector 70 includes a pair of hose connectors 72 which extend from openings (not shown) through the base 76 of slide connector 70. The openings are formed in much the same manner as openings 44 formed in connector 40 and also include sealing mechanisms and methods used in conjunction with connector 40 and seal 50, such as O-rings, gaskets etc. to also prevent leakage from hoses attached to hose connectors 72, as well as to prevent the loss of prime in the components attached to those hoses when slide connector is in the position on seal tray 80 shown in FIGS. 1 and 2.

Figure 3:
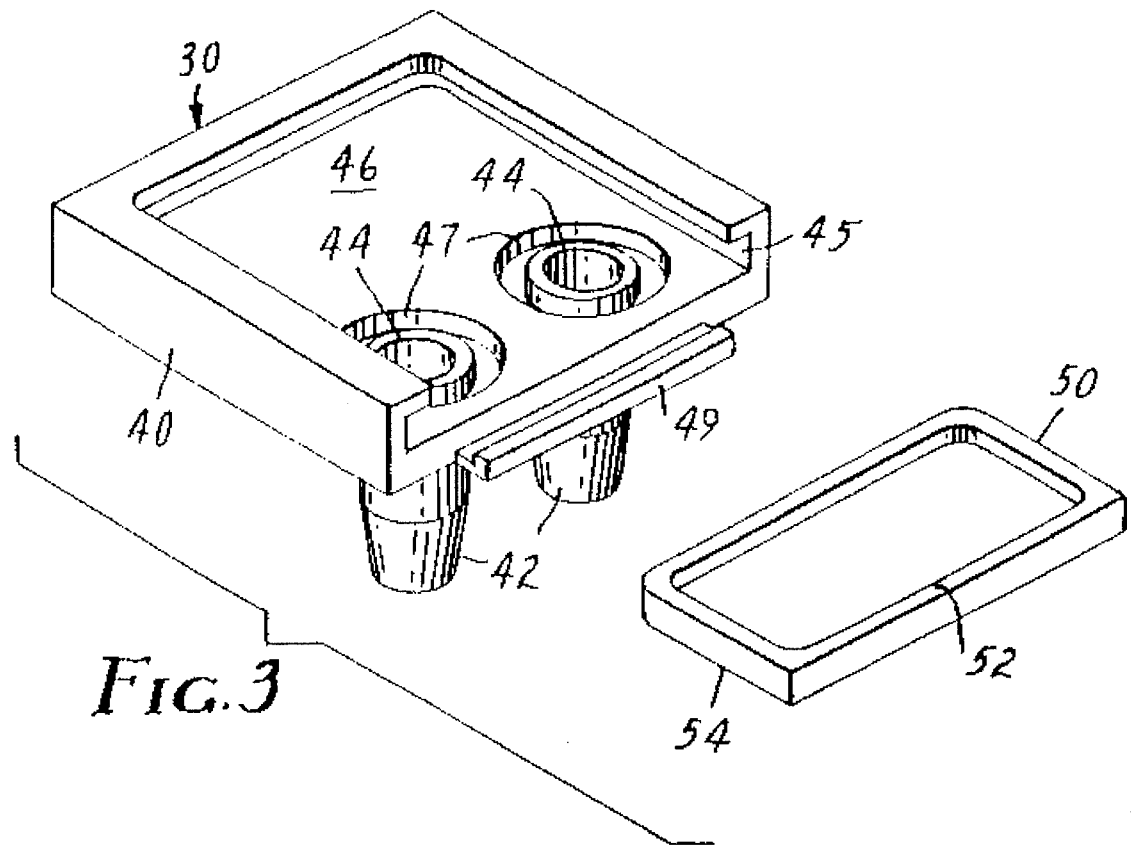
FIG. 3 is an exploded view of a portion of the apparatus depicted in FIG. 1.
Figure 4:
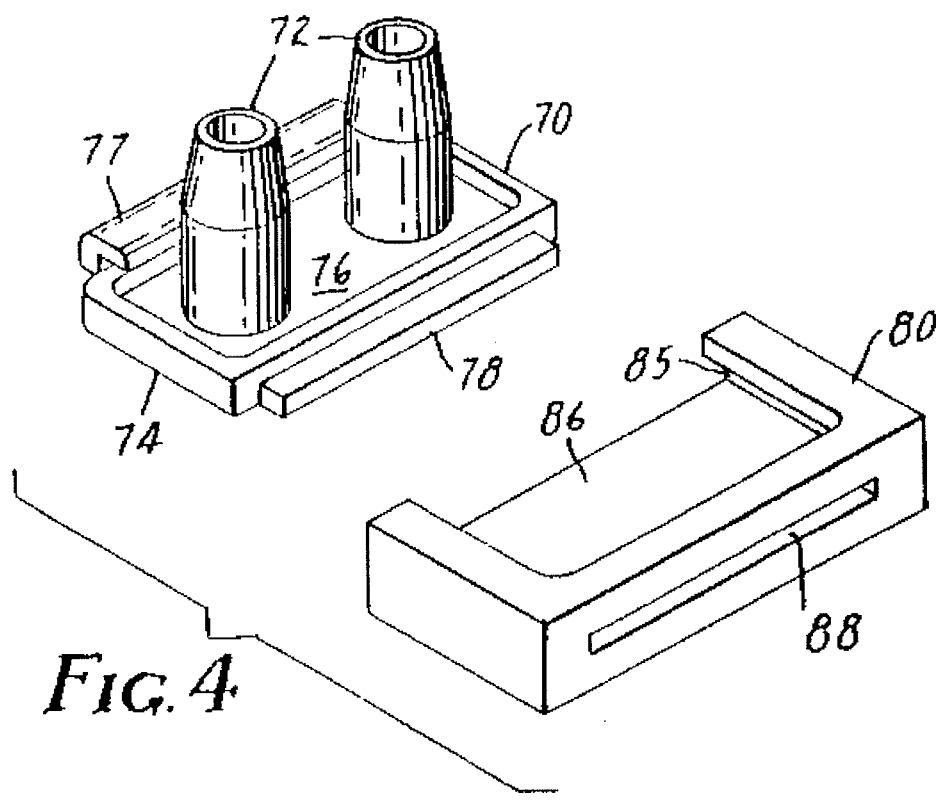
FIG. 4 is an exploded view of the remaining portions of the apparatus depicted in FIG. 1 which are not presented in FIG. 3.

Connector 40 includes a capture mechanism 49 as best seen in FIG. 3, which is designed to mate with a corresponding slot or groove formed in the bottom surface of the seal tray 80 when attached to connector 40. Slide connector 70 preferably includes a capture mechanism 77 designed to capture a lip 52 on seal 50 when seal tray 80 is attached to connector 40.

When assembled as shown in FIG. 1, the slide connector 70 and seal tray 80 form an assembly 60 (see FIG. 2) in which capture mechanism 49 captures seal tray 80 while capture mechanism 77 on slide 70 captures seal 50 using its lip 52. As a result, slide connector 70 can be moved along the tracks 45 and 85 formed in both the seal tray 80 and connector 40, respectively, and seal 50 will always move in conjunction with slide connector 70.

It will be appreciated that the capture mechanisms depicted could be reversed in that the seal tray 80 could be provided with the capture mechanism and, similarly, seal 50 could connect to slide 70 such that the seal 50 and slide 70 move together as a unit when seal tray 80 is attached to connector 40. Furthermore, it will be appreciated that any equivalent mechanism or method useful to accomplish the interlocking functions described above could be substituted for the preferred embodiments disclosed.

Slide connector 70 includes a retainer bar 78 fitted to extend through slot 88 formed in seal tray 80 when slide connector 70 is located on seal tray 80. Retainer bar 78 is flush with the surface of slide connector 70 which faces seal tray 80. Retainer bar 78 retains the seal tray 80 in its proper position with respect to connector 40 when slide connector 70 is moved into its second position, where it is located substantially on connector 40. Retainer bar 78 accomplishes that function by forcing seal tray 80 "downward" against capture mechanism 49 on connector 40.

Maintaining proper positioning, i.e., intimate contact, between the seal tray 80 and connector 40 is important to prevent leakage and/or loss of prime in the components attached to slide connector 70 and connector 40 as the slide connector 70 is moved over the junction between the seal tray 80 and the connector 40. In some instances, it may be desirable to provide a seal between the abutting portions of seal tray 80 and connector 40 to offer additional protection against leakage and/or loss of prime.

Thus, slide connector 70 can be moved into a second position over openings 44 formed in connector 40 such that hoses connected to hose connectors 42 will be in fluid communication with hoses connected to hose connectors 72 on slide connectors 70. When it is desired to replace a component connected to a medical fluid circulating system by the apparatus 10 and associated hoses, slide connector 70 can be moved back into its first position on seal tray 80. After that action has been completed, the openings 44 are sealed by seal 50 which is automatically moved into position over openings 44. Likewise, slide connector 70 and its associated openings are also automatically sealed by seal tray 80 by that action.

As discussed above, when proper sealing is provided between all the elements of apparatus 10, leakage and/or loss of prime can be prevented during changeovers using the apparatus according to the present invention.

An additional feature which may be provided in apparatus 10 is the addition of means for positively indicating when the slide connector 70 is in either its first position on the seal tray 80 or in its second position in which the hose connectors 72 on slide connector 70 are in fluid communication with the hose connectors 42 on the connector 40. In the preferred embodiment, the slide connector 70 is forced against the backstop formed by the portion of track 85 located on the end of seal tray 80 when the slide connector is in its first position.

Due to the capture mechanisms 49 and 77 which operatively connect seal 50 and slide connector 70 and to connect the seal tray 80 to connector 40, the positioning of seal 50 over openings 44 in the connector 40 is insured when the slide connector 70 is in its first position. The movement of slide connector 70 into its second position is positively indicated when seal 50 is forced against the backstop formed by the portion of track 45 on located on the end of connector 40.

Alternate means of indicating positioning may include detents formed between the seal 50 and connector 40 and/or detents formed between the slide connector 70 and seal tray 80. In any such system, the detents would provide physical feedback to the user and, in a more preferred system, the detents would also provide an audible indication of positioning as well.

Although movement of the seal 50 on connector 40 and slide connector 70 on seal tray 80 and connector 40 is linear in the preferred embodiment, it will be understood that the apparatus could rely on rotational motion to bring the necessary parts into and out of alignment as needed and that the present invention should not be limited to linear quick connect apparatus.

Furthermore, although the movement has been shown as involving actual physical manipulation of components such as the seal 50 and slide connector 70 of the preferred apparatus 10, it will be understood that various mechanical systems could be used to move either or both of the seal 50 and slide connector 70. Systems which may be employed include a toothed pinion and rack which translates rotation into linear motion or any other arrangement calculated to move the necessary components. Such a system may prove easier to operate by providing a mechanical advantage to the user which could ease the difficulty of sliding the seal 50 and/or slide connector 70 which may exhibit a relatively high level of friction due to the seals necessary to prevent leakage and/or loss of prime in the systems.

Although the preferred embodiment is described herein as connecting two fluid lines, it will be appreciated that any number of fluid connections could be made including a single connection, and that such variations are considered to fall within the scope of the present invention.

The apparatus according to the present invention is preferably manufactured from any variety of medical grade plastic material such as polycarbonates or similar materials. It is preferred that any material chosen be easily sterilized.

Figure 5:
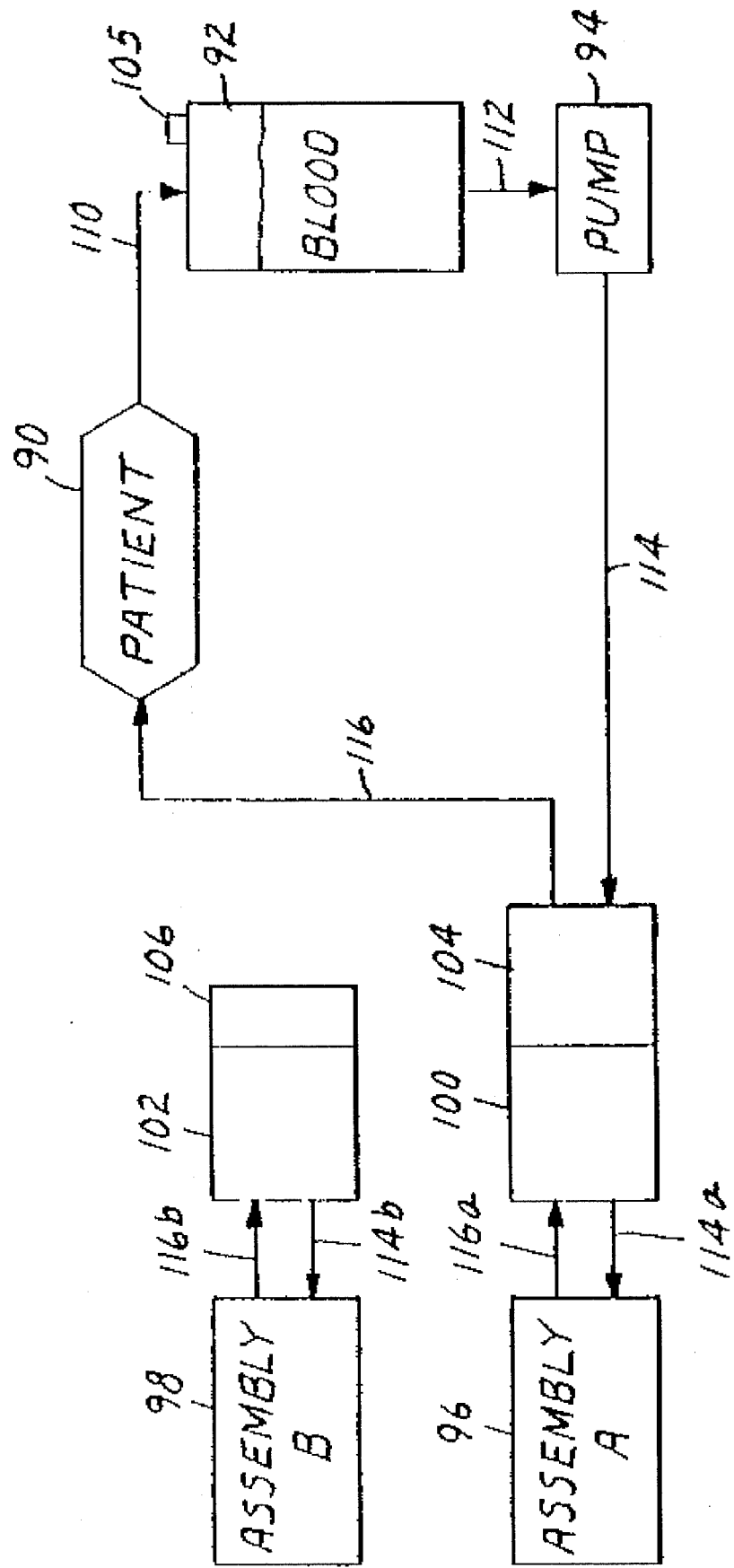
FIG. 5 is a schematic diagram of one system incorporating one in-line quick connect apparatus according to the present invention.

FIG. 5 depicts a schematic diagram of one fluid circulating system in which the quick-connect apparatus according to the present invention can be advantageously used. The system includes a patient 90 from which blood is collected through fluid line 110 in reservoir 92. That reservoir feeds into fluid line 112, which feeds a blood pump 94 pumping blood through line 114 into a quick connect fitting 104 manufactured according to the present invention. Quick connect fitting 104 is connected to the mating quick connect fitting 100 which is used to connect line 114 to line 114a which is, in turn, connected to Assembly A, denoted by reference number 96. As a result, blood pump 94 can pump blood into Assembly A through line 114 and 114a.

Assembly A will typically comprise a heat exchanger/oxygenator and arterial blood filter assembly, but could alternatively comprise a hemodialyzer or any other means for treating blood.

After the blood has been routed through Assembly A, it is returned to quick connect fitting 100 through line 116a. Fitting 100 is connected to quick connect fitting 104 which, in turn, connects to line 116 which returns the treated blood to the patient.

The preferred embodiment of the mating quick connect fittings 100 and 104 preferably comprise a quick connect apparatus 10 as depicted in FIG. 1 through 4. It is unimportant as to which of the connectors 100 and 104 corresponds to connector 40 and seal tray 80/slide connector 70, as any arrangement will provide the necessary quick connect capabilities to connect line 114 to line 114a and line 116 to line 116a.

In many instances, it is necessary or desirable to replace Assembly A (96) with a replacement Assembly B (98) due to leakage, clogging or any other situation in which the performance of Assembly A falls below acceptable levels. Alternatively, it may be desired to replace Assembly A with an Assembly B which performs a different function. It is in either situation, both of which require the disconnection and reconnection of components, in which the present invention provides the advantages discussed above.

Assembly B is preferably provided pre-primed with saline solution such that it is ready to use by the medical personnel with no additional preparation. Likewise, the present invention allows the remainder of the system, i.e., the reservoir 92, fluid line 112, blood pump 94, and fluid lines 114 and 116 to be pre-primed prior to cannulating the patient's heart, thereby further simplifying the setup and use of a blood circulating system as well as reducing the risk of entraining air into the lines.

Pre-priming is accomplished by using a shunt connector (not shown) in which the hose connectors are attached to each other by, for example, a short piece of hose. To pre-prime the system prior to cannulating, the shunt connector would be attached to quick connect fitting 102, thereby placing line 114 in fluid communication with line 116.

Assembly B includes a set of hoses 114b and 116b which terminate in a quick connect fitting 102 which is of the same construction as fitting 100 on Assembly A. Quick connect fitting 102 is provided with a seal 106 as shown in FIG. 5. Seal 106 preferably comprises a device similar to seal 50 or seal tray 80, both of apparatus 10 as depicted in FIGS. 1–4. The exact construction depends on the mating requirements of fitting 102 with fitting 104.

When the changeover is performed, quick connect fitting 104 is disconnected from quick connect fitting 100 and both fittings 100 and 104 are automatically sealed as described with reference to apparatus 10 described above. By automatically sealing, the lines connected to both fittings 100 and 104 are prevented from leaking, air is prevented from entering the fluid lines and prime within the system is maintained.

Quick connect fitting 104 is then connected to quick connect fitting 102 attached to Assembly B. Seal 106 is automatically removed from fitting 102 in a way in which prime is maintained in Assembly B (assuming that it was provided pre-primed). As a result, the in-line quick connect apparatus according to the present invention provides the ability to efficiently and safely replace components in the blood circulating system.

An additional feature of the system depicted in FIG. 5 is the provision of a quick connect fitting 105 on the reservoir 92. Quick connect fitting 105 mates with quick connect fittings 100 and 102 in the same manner as do quick connect fittings 104 and 106 described above and is constructed the same as those fittings.

In use, quick connect fitting 105 allows the medical personnel to quickly and safely drain blood or any other medical fluid within either of the Assemblies A or B after use. To do so, the appropriate quick connect fitting 100 or 102 is attached to quick connect fitting 105 on reservoir 92 and the assembly is elevated, thereby causing blood to flow into the reservoir 92. After the drainage process is complete, the quick connect fitting 100 or 102 is removed from quick connect fitting 105, with both portions being automatically sealed after disconnection as discussed above.

Although only one set of quick connect fittings is used in the system depicted in FIG. 5, it will be understood that versions of the quick connect apparatus according to the present invention could be used in multiples to connect all or some of the components in the system together. For example, the reservoir and pump could be connected to the system using the apparatus of the present invention, thereby allowing quick changeovers of those components too, in addition to the changeovers between Assemblies A & B as described above.

It will be understood that various changes could be made in the above described constructions without departing from the scope of the present invention. It is intended that all matter contained in the above description or shown in the accompanying drawings shall be interpreted only as illustrative of the present invention and not in a limiting sense.

I claim:

1. An in-line quick connect apparatus for changeovers in medical fluid lines, said apparatus comprising:

a first assembly comprising:

a first connector having a connector opening and first connector means for mounting tubing in fluid communication with the connector opening;

a seal slidably mounted on said first connector, said seal being movable between a first position wherein said connector opening is sealed by said seal and a second position wherein said connector opening is not sealed by said seal; and, first track means on said first connector for guiding movement of said seal along the first track means between the first and second positions; and a second assembly comprising:

a seal tray removably attachable to said first connector;

a slide connector slidably mounted on said seal tray, said slide connector having a slide opening and second connector means for mounting tubing in fluid communication with the slide opening; and second track means on said seal tray for guiding movement of said slide connector, said second track means being in alignment with said first track means on said first connector when said seal tray is attached to said first connector, said slide connector being movable along the second track means and first track means between:

a first position in which the slide connector is held by the second track means and said slide opening is sealed against said seal tray; and a second position in which the slide connector is held by the first track means and said slide opening is in fluid communication with said connector opening of the first connector;

said connector opening of the first connector and said slide opening of the slide connector remaining sealed during movement of said slide connector and said seal between their respective first and second positions.

2. An apparatus according to claim 1, wherein said slide connector is operatively connected to said seal when said seal tray is attached to said first connector, such that said seal and said slide move together along said first and second track means.

3. An apparatus according to claim 1, wherein said slide connector is located on said first connector when in said second position and includes means for retaining the seal tray attached on the first connector when the slide connector is in its second position.

4. An in-line quick connect apparatus for changeovers in medical fluid lines, said apparatus comprising:

a) a connector having a connector opening:

b) a seal movably attached to said connector, said seal being movable into a first position wherein said connector opening is sealed by said seal and a second position wherein said connector opening is not sealed by said seal;

c) first track means on said connector for guiding movement of said seal;

d) a seal tray removably attached to said connector;

e) a slide connector movably attached to said seal tray, said slide connector having a slide opening; and f) second track means on said seal tray for guiding movement of said slide connector, said second track means being in alignment with said first track means on said connector when said seal tray is attached to said connector, wherein said slide connector is movable between a first position in which said slide opening is sealed against said seal tray and a second position in which said slide opening is in fluid communication with said connector opening, and further wherein said connector opening and said slide opening remain sealed during movement of said slide connector and said seal between their respective said first and second positions;

said slide connector being located on said connector when in said second position;

said slide connector further comprises means for retaining said seal tray attached to said connector when said slide connector is in said second position.

5. An apparatus according to claim 4, further comprising means for positively indicating when said slide connector is in either of said first and second positions.

6. An apparatus according to claim 5, wherein said means for positively indicating when the slide connector is in either of its first and second positions comprises a detent.

7. An in-line quick connect apparatus for changeovers in medical fluid lines, said apparatus comprising:

a first assembly comprising:

a first connector having a connector opening and first connector means for mounting tubing in fluid communication with the connector opening;

a seal slidably mounted on the first connector for movement between a first position wherein said connector opening is sealed by said seal and a second position wherein said connector opening is not sealed by said seal; and first track means on said first connector for guiding movement of said seal along the first track means between the first and second positions; and a second assembly comprising:

a seal tray removably attachable to said first connector;

a slide connector slidably mounted on the seal tray, said slide connector having a slide opening and second connector means for mounting tubing in fluid communication with the slide opening;

second track means on said seal tray for guiding movement of said slide connector along the second track means and onto the first track means, said second track means being in alignment with said first track means on said first connector when said seal tray is attached to said first connector, said slide connector being movable between:

a first position in which the slide connector is held by the second track means and said slide opening is sealed by said seal tray; and a second position in which said slide connector is held by the first track means of said first connector and said slide opening is in fluid communication with said connector opening;

said slide connector being operatively connected to said seal when said seal tray is attached to said first connector, such that said seal and said slide move together along said first and second track means;

said connector opening and said slide opening remaining sealed during movement of said slide connector and said seal between their respective said first and second positions; and means for retaining said seal tray attached to said first connector when said slide connector is in said second position.

8. A medical fluid circulating system comprising:

a) a source of medical fluid;

b) a component in said system, said medical fluid flowing through said component;

c) a first fluid line transporting said medical fluid away from said source and towards said component;

d) an in-line quick connect apparatus for sealing and disconnecting said first fluid line; said apparatus comprising:

1) a first assembly comprising:

a first connector having a connector opening in fluid communication with said first fluid line;

a seal slidably mounted on the first connector, said seal being movable between a first position wherein said connector opening is sealed by said seal and a second position wherein said connector opening is not sealed by said seal;

first track means on said first connector for guiding movement of said seal along the first track means between the first and second positions; and 2) a second assembly comprising:

a seal tray removably attachable to said first connector;

a slide connector movably attached to said seal tray, said slide connector having a slide opening in fluid communication with said first fluid line;

second track means on said seal tray for guiding movement of said slide connector along the second track means and onto the first track means of the first connector, said second track means being in alignment with said first track means on said first connector when the seal tray is attached to the first connector, said slide connector being movable along the second track means and onto the first track means of the first connector between:

a first position in which the slide connector is held by the second track means and said slide opening is sealed by said seal tray; and a second position in which the slide connector is held by the first track means and said slide opening is in fluid communication with said connector opening;

said connector opening and said slide opening remaining sealed during movement of said seal and said slide connector between their respective said first and second positions.

9. A system according to claim 8, wherein said slide connector is operatively first connected to said seal when said seal tray is attached to said connector, such that said seal and said slide connector move together along said first and second track means.

10. A system according to claim 8, wherein said medical fluid is blood and said source is a patient.

11. A medical fluid circulating system comprising:

a) a source of medical fluid;

b) a component in said system, said medical fluid flowing through said component;

c) a first fluid line transporting said medical fluid away from said source and towards said component;

d) an in-line quick connect apparatus for sealing and disconnecting said first fluid line; said apparatus comprising:

1) a connector having a connector opening, said connector opening in fluid communication with said first fluid line;

2) a seal movably attached to said connector, said seal being movable into a first position wherein said connector opening is sealed by said seal and a second position wherein said connector opening is not sealed by said seal;

3) first track means on said connector for guiding movement of said seal;

4) a seal tray removably attached to said connector;

5) a slide connector movably attached to said seal tray, said slide connector having a slide opening in fluid communication with said first fluid line;

6) second track means on said seal tray for guiding movement of said slide connector, said second track means being in alignment with said first track means on said connector, wherein said slide connector is movable between a first position in which said slide opening is sealed by said seal tray and a second position in which said slide opening is in fluid communication with said connector opening, and further wherein said connector opening and said slide opening remain sealed during movement of said seal and said slide connector between their respective said first and second positions;

the system further comprising:

e) an alternate component;

f) alternate first fluid line in fluid communication with said alternate component;

g) an alternate seal tray adapted for removable attachment to said connector in place of said seal tray;

h) an alternate slide connector movably attached to said alternate seal tray, said alternate slide connector having a connector opening in fluid communication with said alternate first fluid line;

i) alternate second track means on said alternate seal tray for guiding movement of said alternate slide connector, said alternate second track means being in alignment with said first track means when said alternate seal tray is attached to said connector, wherein said alternate slide connector is movable between a first position in which said alternate slide opening is sealed by said alternate seal tray and a second position in which said alternate slide opening is in fluid communication with said connector opening, and further wherein said alternate connector opening and said alternate slide opening remain sealed during movement of said alternate slide connector between said first and second positions.

12. A medical fluid circulating system comprising:
   a) a source of medical fluid;
   b) a component in said system, said medical fluid flowing through said component;
   c) a first fluid line transporting said medical fluid away from said source and towards said component;
   d) an in-line quick connect apparatus for sealing and disconnecting said first fluid line; said apparatus comprising:
      1) a connector having a connector opening, said connector opening in fluid communication with said first fluid line;
      2) a seal movably attached to said connector, said seal being movable into a first position wherein said connector opening is sealed by said seal and a second position wherein said connector opening is not sealed by said seal;
      3) first track means on said connector for guiding movement of said seal;
      4) a seal tray removably attached to said connector;
      5) a slide connector movably attached to said seal tray, said slide connector having a slide opening in fluid communication with said first fluid line;
      6) second track means on said seal tray for guiding movement of said slide connector, said second track means being in alignment with said first track means on said connector, wherein said slide connector is movable between a first position in which said slide opening is sealed by said seal tray and a second position in which said slide opening is in fluid communication with said connector opening, and further wherein said connector opening and said slide opening remain sealed during movement of said seal and said slide connector between their respective said first and second positions;

the system further comprising a second fluid line transporting said medical fluid away from said component and towards said source, and further wherein said in-line quick connect apparatus further comprises a second connector opening in fluid communication with an upstream portion of said second fluid line, said seal sealing said second connector opening when said seal is in said first position, and yet further wherein said slide connector further comprises a second slide opening in fluid communication with a downstream portion of said second fluid line, said second slide opening sealed by said seal tray when said slide connector is in said first position, and still further wherein said second connector opening and said second slide opening remain sealed during movement of said seal and said slide connector between their respective said first and second positions.

13. A system according to claim 12, wherein said medical fluid is blood and said source is a patient.

14. A system according to claim 13, wherein said component comprises means for treating said blood.

15. A system according to claim 14, wherein said means for treating comprises a blood oxygenator and heat exchanger assembly.

16. A system according to claim 12, further comprising:
   a) an alternate component;
   b) alternate first and second fluid lines in fluid communication with said alternate component;
   c) an alternate seal tray adapted for removable attachment to said connector in place of said seal tray;
   d) an alternate slide connector movably attached to said alternate seal tray, said alternate slide connector having at least two openings, a first of said alternate slide openings in fluid communication with said alternate first fluid line and a second of said alternate slide openings in fluid communication with said alternate second fluid line;
   e) alternate second track means on said alternate seal tray for guiding movement of said alternate slide connector, said alternate second track means being in alignment with said first track means when attached to said connector, wherein said alternate slide connector is movable between a first position in which said alternate slide openings are sealed by said alternate seal tray and a second position in which said first alternate slide opening is in fluid communication with said first connector opening and said second alternate slide opening is in fluid communication with said second connector opening, and further wherein said alternate connector openings and said alternate slide openings remain sealed during movement of said alternate slide connector between said first and second positions.

* * * * *

UNITED STATES PATENT AND TRADEMARK OFFICE
CERTIFICATE OF CORRECTION

PATENT NO. : 5,542,913
DATED : August 6, 1996
INVENTOR(S) : Erin J. Lindsay

It is certified that error appears in the above-indentified patent and that said Letters Patent is hereby corrected as shown below:

Title page "Related U.S. Application Data" [63] delete "Continuation-in-part of Ser. No. 77,344, June 19, 1993, Pat. No. 5,399,156, which is a continuation-in-part of Ser. No.493,491, June 15, 1929, abandoned, which is a continuation-in-part of Ser. No. 493,286, March 14, 1990, Pat. No. 5,149,318" and insert --Continuation-in-part of Ser. No. 77,344, June 14, 1993, Pat. No. 5,399,156, which is a continuation-in-part of Ser. No. 898,491, June 15, 1992, abandoned, which is a continuation-in-part of Ser. No. 493,286, March 14, 1990, Pat. No. 5,149,318--

Signed and Sealed this

Twenty-fourth Day of February, 1998

*Attest:*

BRUCE LEHMAN

*Attesting Officer*  *Commissioner of Patents and Trademarks*